United States Patent
Hansen

(10) Patent No.: US 12,307,559 B2
(45) Date of Patent: May 20, 2025

(54) DEVICE AND METHOD FOR PET IMAGE ANALYSIS AND RECONSTRUCTION

(71) Applicant: Aarhus Universitet, Aarhus C (DK)

(72) Inventor: Thomas Mejer Hansen, Knebel (DK)

(73) Assignee: Aarhus Universitet, Aarhus C (DK)

( * ) Notice: Subject to any disclaimer, the term of this patent is extended or adjusted under 35 U.S.C. 154(b) by 334 days.

(21) Appl. No.: 17/906,726

(22) PCT Filed: Mar. 22, 2021

(86) PCT No.: PCT/EP2021/057275
§ 371 (c)(1),
(2) Date: Sep. 19, 2022

(87) PCT Pub. No.: WO2021/191151
PCT Pub. Date: Sep. 30, 2021

(65) Prior Publication Data
US 2023/0154068 A1   May 18, 2023

(30) Foreign Application Priority Data
Mar. 24, 2020   (EP) .................................... 20165234

(51) Int. Cl.
*G06T 11/00*   (2006.01)
*A61B 6/03*   (2006.01)

(52) U.S. Cl.
CPC ............ *G06T 11/006* (2013.01); *A61B 6/037* (2013.01)

(58) Field of Classification Search
CPC .............................. G06T 11/006; A61B 6/037
See application file for complete search history.

(56) References Cited

U.S. PATENT DOCUMENTS

| | | | |
|---|---|---|---|
| 9,069,100 B2 | 6/2015 | Kolbjørnsen et al. | |
| 2013/0188854 A1* | 7/2013 | Bilgic | A61B 5/055 382/131 |
| 2015/0145885 A1* | 5/2015 | Krol | G06T 11/006 345/618 |
| 2018/0005412 A1* | 1/2018 | Ma | G06T 11/008 |

(Continued)

FOREIGN PATENT DOCUMENTS

| | | | | |
|---|---|---|---|---|
| CN | 102324089 B | * | 4/2013 | |
| CN | 103559728 B | * | 5/2017 | |
| CN | 110009707 A | * | 7/2019 | .......... G06T 11/005 |

(Continued)

OTHER PUBLICATIONS

International Preliminary Report on Patentability issued Sep. 22, 2022 in International Application No. PCT/EP2021/057275.

(Continued)

*Primary Examiner* — Ted W Barnes
(74) *Attorney, Agent, or Firm* — Knobbe Martens Olson & Bear LLP

(57) ABSTRACT

A device and a method for image reconstruction for medical imaging is provided. The method comprises obtaining a lookup table of pre-computed sets of data, obtaining a PET image, dividing the PET image into subset-images of one, or more, pixels. For each subset-image of pixels in the PET image, an extended rejection sampler is used to select model-images from the lookup table, determining and outputting a representation image based on the posterior distribution.

13 Claims, 12 Drawing Sheets

(56) References Cited

U.S. PATENT DOCUMENTS

2019/0035118 A1    1/2019    Zhao et al.
2020/0202589 A1*  6/2020    Hansen ................ A61B 6/5205

FOREIGN PATENT DOCUMENTS

| | | | | |
|---|---|---|---|---|
| CN | 110717951 B | * | 8/2021 | ........... G06K 9/6256 |
| WO | WO 2018/215357 A1 | | 11/2018 | |
| WO | WO-2019090533 A1 | * | 5/2019 | ........... A61N 5/1039 |

OTHER PUBLICATIONS

AGU-SEG Airborne Geophysics Workshop, "Fast probabilistic inversion of AEM data using approximate rejection sampling", Davie, Florida, Jun. 11-13, 2019, abstract.

Hansen et al., "Accounting for imperfect forward modeling in geophysical inverse problems—Exemplified for crosshole tomography", Geophysics, vol. 79, No. 3 (May-Jun. 2014); p. H1-H21.

Hansen et al., "Probabilistic Integration of Geo-Information", Integrated Imaging of the Earth: Theory and Applications, Geophysical Monograph 218, First Edition, American Geophysical Union, published 2016 by John Wiley & Sons, Inc.

Hansen et al., "Probabilistic restoration of PET—Potential for Resolution Enhancement", Submitted to: Phys. Med. Biol., 27 pages.

Kontaxakis et al., "Maximum Likelihood Algorithms for Image Reconstruction in Positron Emission Tomography", Radionuclides for Oncology—Current Status and Future Aspects, Mediterra Publishers, Athens, 1998, pp. 73-106.

Lewitt et al., "Overview of Methods for Image Reconstruction From Projections in Emission Computed Tomography", Proceedings of the IEEE, vol. 91, No. 10, Oct. 2003.

Metropolis et al., "Equation of State Calculations by Fast Computing Machines", The Journal of Chemical Physics, vol. 21, No. 6, Jun. 1953, in 6 pages.

Mosegaard et al., "Monte Carlo sampling of solutions to inverse problems", Journal of Geophysical Research, vol. 100, No., B7, p. 12,431-12,447, 1995.

Shepp et al., "Maximum Likelihood Reconstruction for Emission Tomography", IEEE Transactions On Medical Imaging, vol. MI-1, No. 2, Oct. 1982.

Tarantola et al., "Inverse Problems = Quest for Information", J. Geophys. (1982) 50:159-170.

\* cited by examiner

DEVICE AND METHOD FOR PET IMAGE ANALYSIS AND RECONSTRUCTION

CROSS REFERENCE TO RELATED APPLICATIONS

This application is a U.S. National Phase Application of PCT International Application Number PCT/EP2021/057275, filed on Mar. 22, 2021, designating the United States of America and published in the English language, which is an International Application of and claims the benefit of priority to European Patent Application No. 20165234.4, filed on Mar. 24, 2020. The disclosures of the above-referenced applications are hereby expressly incorporated by reference in their entireties.

FIELD OF THE INVENTION

The present invention relates to image analysis and reconstruction for medical imaging and in particular to a device and a method of position emission tomography (PET) image reconstruction.

BACKGROUND OF THE INVENTION

The use of image reconstruction, enhancement and analysis are widely used on images related to medical scanners. For example, in PET scanning a radioactive tracer is injected into a patient and it is constructed such that cancer cells will accumulate the tracer material. A PET scanner is then used to record the radioactive decay, and provide a reconstructed PET image representing the in-situ distribution of tracer intensity. A high tracer intensity can be indicative of cancer lesions.

However, the PET image is contaminated by blurring and noise, related to how the PET data has been recorded.

Clinical oncology is heavily exploiting positron emission tomography (PET) searching for, monitoring and imaging tumours and metastases. In diagnostics, monitoring and research medical imaging techniques are increasingly used. PET scanning is also used as an important tool for clinical diagnosis of brain diseases and in general for mapping heart function and brain of humans.

Continuous efforts are made to increase the image quality of medical images and in particular, PET image processing methods, however improving the image quality of PET images is still desired.

Hence, an improved image reconstruction would be advantageous, and in particular, a more efficient and/or reliable method for image reconstruction would be advantageous.

WO2018/215357 Disclosed is a device and a method for medical image reconstruction. The method comprises obtaining image data of a medical scanner; obtaining a noise model for the image data from the medical scanner; obtaining an initial model indicative of expected image data properties; obtaining a mapping, wherein the mapping is indicative of a mapping from the medical scanner; determining a set of candidate images based on the image data, the noise model, the initial model, and the mapping; and determining and outputting a first representation of the image data based on the set of candidate images.

A Bayesian approach to image reconstruction can be posed as a probabilistic inverse problem.

See the reference: Tarantola, A., & Valette, B. (1982). Inverse problems=quest for information. Journal of geophysics, 50(1), 159-170.

In the Bayesian approach prior information, quantified through a prior probability density $\rho(m)$, of the expected tracer intensity is combined with a description of how well the forward response of the model fits observed data, as quantified through the likelihood function, $L(m)$. The general solution to the probabilistic/Bayesian formulation of an inverse problem is a probability density, the posterior probability density $\sigma(m)$.

$$\sigma(m) = \rho(m) * L(m) \tag{1}$$

Except for linear Gaussian inverse problems, an analytical description of $\sigma(m)$ is not feasible. Instead, Markov chain Monte Carlo based sampling methods, such as the Metropolis-Hastings algorithm, exist that allow sampling of $\sigma(m)$. While guaranteed to in principle sample the correct posterior probability density $\sigma(m)$, such sampling methods become both computationally expensive, to the point where they cannot be practically applied, and the results difficult to interpret.

The Metropolis-Hastings algorithm is described in Metropolis, Nicholas, et al. "Equation of state calculations by fast computing machines." The journal of chemical physics 21.6 (1953): 1087-1092.

The extended Metropolis algorithm is different from the classical variants of the Metropolis-Hastings algorithms, in that one does not need to be able to evaluate $\sigma(m)$ (and hence not $\rho(m)$); it is enough that an algorithm exists that can perform a random walk in the space of a priori possible modes (i.e. than an algorithm can sample $\rho(m)$ through a random walk), and that one can evaluate the likelihood, $L(m)$, for any model.

The extended Metropolis algorithm is described in the reference:

Mosegaard, Klaus, and Albert Tarantola. "Monte Carlo sampling of solutions to inverse problems." Journal of Geophysical Research: Solid Earth 100.B7 (1995): 12431-12447.

The use of the extended Metropolis algorithm has the potential to change the complexity of the sampling problem from a harder problem to an easier problem as the complexity is linked to the number of free parameters of the prior probability density $\rho(m)$, and not the total number of model parameters considered. When a spatially informed prior model is used, the number of free parameters may be much smaller than the actual number of model parameters. Therefore, the use of the extended Metropolis algorithm can be computationally more efficient than traditional Metropolis-Hastings based sampling. However, the method is still CPU intensive. Analysis of $\rho(m)$ for a case considering a 2D PET image slice of 75×115 pixels, took many hours to complete.

OBJECT OF THE INVENTION

It is an object of the present invention to provide an improvement in the speed of making probabilistic image analysis and reconstruction of PET images.

In particular, it may be seen as an object of the present invention to provide a method that solves parts of the above-mentioned problems of the prior art with the same image quality, but faster than known methods of medical images to improve the detectability of tumours.

SUMMARY OF THE INVENTION

Thus, the above-described object and several other objects are intended to be obtained in a first aspect of the invention by providing a faster method for image reconstruction for medical imaging of a subject. The subject can be a human or an animal.

The invention is particularly, but not exclusively, advantageous for obtaining improved detection and identification of tumours. The method is based on collecting expert data and use this data to improve the quality of PET scans of humans or animals.

Here, we present a method, relying on the extended rejection sampler, that allows 1) very fast sampling of independent realizations of the posterior probability density σ(m), 2) analysis the posterior probability density σ(m), here-on referred to as the posterior distribution, and 3) use of arbitrarily complex prior information, here-on referred to as the prior, ρ(m). It is based on using lookup tables of pre-computed sets of models, here-on referred to as model-images m, and data, here-on referred to as data-images d. As this training data set is limited in size, this may lead to a modelling error (but this is not always the case), that is quantified and accounted for.

The best performance is obtained for cases with informed prior information and when applied to 'localized' inverse problems, in which the inverse problem can be applied many times to localized regions of the model parameter and data space. In such cases, the training data set need only be computed once, and only the likelihood (data fit) needs to be computed for each considered data set. A sample of independent realizations of the posterior distribution, as well as summary statistics, can be computed accurately, using only a fraction of the CPU needed when sampling the posterior distribution using a Metropolis type algorithm.

The PET scan, the reconstructed PET image, from here-on referred to as a PET image, $d_{obs}$, can be 2-dimensional or a 3-dimensional image covering parts of a human body. Special for the invention is that the PET image is divided into many small subset-images, $d_{ss}$. A subset-image $d_{ss}$ is a localized image covering a small part of the full PET image, $d_{obs}$. Therefore, the method of this invention is called LoPET.

The Forward Problem

The method relies on an understanding of the physical process that generates the observed PET image, $d_{obs}$.

Say m represent the in situ distribution of tracer intensity. Then the PET image d one will obtain can be described through the following process:

$$d = g(m) + n(m), \quad (2)$$

where 'g' represents a function that applies smoothing and 'n' represent a function that generates noise according to a specific noise model. d represent one example of a PET image that would be observed for a specific model m.

'g' represent the blurring introduced by using a specific type of scanner and reconstruction method, and is related to the point spread function. This is typically represented by a linear operator $G_{PSF}$, such that the forward problem can be described by $$d = G_{PSF}(m) + n(m). \quad (3)$$

The noise model is represented by a probability distribution describing the expected noise in the PET image. It is quantified through a likelihood function $$L(m) = f(g(m) - d_{obs}).$$

I.e. the likelihood function evaluated on a specific model m, express the probability density function value that the data residual for a specific model m is a realization of the noise model.

The likelihood function L(m) describes the distribution of the noise n(m) in (3), and is a measure of the degree of fit between data, in the invention described herein the data-images d, predicted from the model, in the invention described herein from the model-images m, using the g(m) function, and the observed data $d_{obs}$, which in the invention described herein is the subset-images $d_{ss}$. g(m) is a smoothing function and gives the noise free data-image d. The likelihood therefore is a function depending on the degree of fit between the data-image d and the observed data $d_{obs}$, which is the subset-image $d_{ss}$. The data-image d is obtained as d=g(m).

In case a multivariate Gaussian model is, with covariance $C_d$, is chosen to represent the noise, the likelihood L(m) is calculated from the formula $$L(m) = ((2\pi)^2 |C_d|)^{-0.5} \exp(-0.5((d_{obs} - g(m))^T) C_d^{-1} (d_{obs} - g(m))). \quad (4)$$

Note though that any probabilistic model for the noise can be used, as long as L(m) can be evaluated for any model m.

The formulas (2)-(4) apply to both using the full PET image, $d_{obs}$, and a localized part of the PET image, where $d_{obs}$ is the subset-image $d_{ss}$. g(m) may be the linear operator $G_{PSF}(m)$.

In practice, a noise model can be obtained by scanning a known target and computing the residual between the obtained PET image and the known target $m_{target}$. The residual then represents one realization of the noise, from which a statistical model of the noise can be inferred. Similarly, the averaging function $G_{PSF}(m)$ can be obtained by analysing the residual between the obtained PET image $d_{obs}$ and the noise-free forward response of the known target, $g(m_{target})$. For instance if $G_{PSF}$ is characterized by the width w of the averaging function, one can choose w as the value of w that miminizes $\|d_{obs} - G_{PSFw}(m_{target})\|$, where $G_{PSFw}(m_{target})$ is the averaging function with width w.

The Extended Rejection Sampler

The extended rejection sampler is a variant of the classical rejection sampler, where one can sample from the posterior distribution, requiring only that one can sample from the prior and evaluate the likelihood. This algorithm is described in the reference:

Hansen, Thomas Mejer, et al. "Probabilistic integration of geo-information." Integrated imaging of the earth: Theory and applications 218 (2016): 93-116.

The extended rejection sampler can be implemented using the following simple algorithm, that is repeated until enough realization of the posterior distribution is obtained:

1. Propose a model-image m* representing the prior ρ(m),
2. Accept the model-image m* as a realization of the posterior distribution, σ(m), with probability $$P_{acc} = L(m^*) / \max(L(m^*)) \quad (5)$$

Step 1 requires than one can sample from the prior. Step 2 requires than one can solve the forward problem (g(m*)), and evaluate the Likelihood (Eqn. 4).

The extended rejection sampler is very simple to implement, but it is also regarded as an extremely inefficient way to sample the posterior distributions, as most proposed models will have a very small probability of being accepted. Further, the application of the extended rejection sampler is hampered by the fact the one must know the maximum possible value of the likelihood, max(L(m*)), that one can expect. This is in general not known and leads to an even more inefficient algorithm.

The main idea of LoPET is to compute a set of realizations, in form of the sample M*, from the prior only once and store them in a lookup table. Also, for any model in the lookup table, the forward response is computed once, and stored in a lookup table. Then, when applying the extended rejection sampler for a specific observed data, one only needs to compute the likelihood function based on the lookup table. max(L(m*)) is then trivially obtained. The LoPET algorithm can then be efficiently applied on local subsets, subset-images $d_{ss}$, of the full PET image $d_{obs}$.

The Prior $\rho(m)$

The first step in the invention is to use the collected expert data to create a prior $\rho(m)$. The prior represents prior knowledge about the model parameters. This can come from expert knowledge, previous surveys and similar sources.

An expert, for instance a doctor working with diagnosing cancer from PET images, can make expert data, usually in cooperation with a data specialist. The expert creates or selects, for instance, a set of images for the expert data. The images the expert selects can be images from humans showing tumours or metastases or other kinds of relevant cell structures. Based on the expert data a data specialist generates a statistical model, representing the prior information, describing the variation in these images.

Alternatively, the data specialist can generate the prior from previous surveys or other data sources.

Methods to quantify and sample from a prior is described in the references:

Deutsch, C. V., & Journal, A. G. (1992). Geostatistical software library and user's guide. New York, 119(147).

Mariethoz, G., & Caers, J. (2014). Multiple-point geostatistics: stochastic modeling with training images. John Wiley & Sons.

The prior $\rho(m)$ does not need to exist as a mathematical model (while it can) but is instead represented by the choice of algorithm and geostatistical model. The explicit choice of prior information is then quantified through the realizations generated by the algorithm and geostatistical model of choice.

The Sample M* and Model-Images m*

The example images generated are realizations of the prior and are called model-images, denoted by m*, and they form the sample M*. When completed the sample M* comprises a large number of model-images m*, distributed according to $\rho(m)$. The sample M* includes a high number of model-images m*. The sample M* can include 1000 or 10000 or 100000 or any other suitable numbers of model-images m*.

The sample M* is pre-computed and only created once. When created the model-image m* from the sample M* are placed in a lookup table. The number of sets of data in the lookup table will be denoted $N_I$.

A model-image m, as well as a subset-image $d_{ss}$, is a representation of a small image including 1 pixel, or 10 or 100 or 1000 or any other suitable number of pixels. The pixels can be placed in a 3-dimensional configuration for instance in an image of 9×9×9 pixels or a 2-dimensional configuration for instance in an image of 9×9 pixels.

The number of pixels in a model-image m may be larger than the number of pixels in a subset-image $d_{ss}$ or a data-image d. For instance one pixel in the subset-image $d_{ss}$ or the data-image d may correspond to 4 or 9 or 16 or any other suitable number of pixels in the model-image m.

The number of pixels represented in a model-image m will be denoted $N_M$. A model-image $m=[m_1, m_2, \ldots, m_{N_M}]$ is a vector representing $N_M$ model parameters representing the real tracer intensity in the $N_M$ pixels. That is, if m represents an image of for instance 9×9 pixels, a total of 81 pixels, and m is therefore in this example a vector with $N_M=81$. Likewise for the subset-image $d_{ss}$ or a data-image d.

m denotes a model-image in general, m* denotes a model-image from the sample M* included in the lookup table.

The Sample D*

For each set model m* in the lookup table the corresponding noise-free data d* is computed by evaluating the noise free forward model $$d^* = G_{psf}(m^*)$$

Thus two columns in the lookup table, M* and D*, with $N_I$ sets of models and data, are available.

The Extended Rejection Sampler with Lookup Tables

Each step of the extended rejection sampler in principle consist of computing 1) a realization of the prior, 2) solving the noise free forward problem, d=g(m), 3) computing the likelihood, and determining whether to accept or not.

However, if a lookup table of sets of [m*,d*] exists, then step 1) and 2) has already been performed, By constructing the lookup table once, one can apply the extended rejection sampler without realizing new models from the prior, and without solving the forward problem. These two steps are typically the most computationally expensive of applying the extended rejection sampler.

Therefore, the rejection sampler using lookup tables can be formulated as

1. Compute the likelihood from all sets of model-images m* and data-images d* in the lookup table
2. Compute the maximum likelihood from all likelihood values, and hence compute $P_{acc,i}$ (i=1:$N_I$) for all model-images m* in the lookup table
3. Generate realizations of the posterior distribution by accepting model-images m* from the lookup table proportional to $P_{acc,i}$ Once a lookup table has been established, (needs only be done once for a specific choice of prior) the extended rejection sampler with lookup tables may be computationally much more efficient, than not using lookup tables.

For a subset-image $d_{ss}$ from the PET image being analysed, a likelihood is calculated for each model-image m* in the sample M*. Then an acceptance probability $P_{acc}$ for each model-image m* is determined (Eqn. 5), and this acceptance probability $P_{acc}$ is used to decide whether to accept the model-image m* and add it to the sample of the posterior distribution or reject it.

The rejection sampler generates a sample of the posterior distribution comprising of a collection of model-images from the lookup table. This collection of mode-images, representing the posterior distribution, are used to create a representation image as the output of the method of this invention. This representation image is an image based on pixel representations from the posterior distribution.

Accordingly, a computer-implemented method for image reconstruction for medical imaging of a subject is provided. The subject typically is a human, but can also be an animal. The method comprising:

obtaining a lookup table of pre-computed sets of data, each pre-computed set of data comprises a model-image m* from a sample M* (collection of model images m*) and a corresponding data-image d*, the model-image m* is a realization from a prior $\rho(m)$, the prior $\rho(m)$ is a statistical model based on expert data, each model-image m* is a representation of an image of one, or more, pixels, the data-image d* is determined based on the model-image m* in the same set of data, each data-image d* is a representation of one, or more, pixels, obtaining a PET image and dividing the PET image into subset-images $d_{ss}$, each subset-image $d_{ss}$ is a representation of one, or more, pixels, using for each subset-image $d_{ss}$ from the PET image an extended rejection sampler to accept model-images m* from the lookup table representing the posterior distribution given the subset-image $d_{ss}$, and determining and outputting a representation image based on the posterior distribution.

The model-images m* in the sample M* generated from the prior ρ(m) is placed in a lookup table in a first column. From each model-image m*, a data-image d* is computed using a function g. The data-image d* is placed in a second column in the lookup table.

A data-image d is a smoothed version of the original model-image m, as quantified through the smoothing operator g or $G_{PSF}$. A model-image m can represent $N_M$ pixels, the same number of pixels as a data-image d and the subset-image $d_{ss}$ represents, but also the model-image m can have more pixels than the data image d and the subset-image $d_{ss}$. That is a model-image m can be represented using finer or more coarse resolution than the resolution of d so that the model-image m have more pixels than the data-image d.

d denotes a data-image in general, d* denotes a data-image from the lookup table.

Each subset-image $d_{ss}$ from the PET image is now processed. For each subset-image $d_{ss}$, a likelihood L(m) is calculated for each set of data in the lookup table.

Accordingly, the method further comprises that for each subset-image $d_{ss}$, a likelihood L(m) is calculated for each pre-computed set of data in the lookup table, wherein L(m*) is a function L(m*)=f(g(m*)−$d_{ss}$) wherein g(m*) is the data-image d*.

L(m) describes data residuals as quantified through the probability distribution f(g(m)−$d_{ss}$).

The extended rejection sampler calculates the acceptance probability $P_{acc}$ for each set of data in the lookup table for the given subset-image $d_{ss}$.

The acceptance probability $P_{acc}$ is a number between 0 and 1 for each set of data in the lookup table for each subset-image $d_{ss}$.

Accordingly, the method further comprises that for each subset-image $d_{ss}$, a probability acceptance $P_{acc}$ is calculated for each pre-computed set of data in the lookup table for the given subset-image $d_{ss}$, based on the likelihood L(m) for this pre-computed set of data for the given subset-image $d_{ss}$ divided by a maximum likelihood max(L) for the given subset-image $d_{ss}$.

Now a posterior distribution for the given subset-image $d_{ss}$ can be selected by the extended rejection sampler. Several sets of data, for instance, 10, 100 or 1000 are selected from the lookup table to the posterior distribution. This is done by the extended rejection sampler running through the lookup table and for each set of data in the lookup table the extended rejection sampler calculates $P_{acc}$ and generates a random number between 0 and 1. $P_{acc}$ and the random number is compared, and if the random number is larger than $P_{acc}$, then the model-image from the lookup table is rejected, but if the random number is smaller than $P_{acc}$, then the model-image from the lookup table is accepted for the posterior distribution for the given subset-image $d_{ss}$. The method is continuously going through the lookup table, starting from the beginning again when the last row is tested until the requested number of model-images for the posterior distribution is selected.

Accordingly, the method further comprises for each subset-image $d_{ss}$ that the probability acceptance $P_{acc}$, calculated for each pre-computed set of data in the lookup table for the given subset-image $d_{ss}$, is used by the extended rejection sampler to determine whether to accept the model-image m* from the pre-computed set of data in the lookup table (20) for a posterior distribution for the given subset-image $d_{ss}$.

A random value is generated for each pre-computed set of data in the lookup table (20) to compare with the probability acceptance $P_{acc}$ to decide whether to accept the model-image m* from the pre-computed set of data in the lookup table (20) for the posterior distribution (82).

When posterior distributions are accepted for all the subset-images $d_{ss}$ in the PET image, the posterior distributions can be used to generate all kind of statistic data for different representations of the data. Including images that will make it easier to detect whether a patient has cancer or not.

Modelling Error

The size of the lookup table will be finite in size. This may introduce an error, as the number of sets of data $N_l$ in the lookup table may not reflect the full span of possible models a priori. On the other hand, if $N_l$ is large enough, then one may use the extended rejection sampler as it is, without modelling error related to the use of a limited set of data. The potential modelling error can be quantified by constructing an approximate error model.

The modelling error is quantified by a statistical model, often Gaussian, that describes the expected data residual ($d_{ss}$−g(m)) due to forward model imperfections.

If the modelling error is Gaussian with mean $d_t$ and covariance $C_t$, and the measurement noise Gaussian with covariance $C_d$, then the likelihood function including the modelling error is defined as $$L(m)=((2\pi)^2|C_d+C_t|^{-0.5}\exp(-\tfrac{1}{2}((d_{obs}-g(m)-d_t)^T)(C_d+C_t)^{-1}(d_{obs}-g(m)-d_t))$$

In this equation, when applied in the invention, $d_{obs}$ is the subset-image $d_{ss}$ and g(m) is d* from the lookup table.

The modelling error can be described by a Gaussian probability density function with the mean $d_t$ and the covariance $C_t$. The measurement uncertainty can be described by the covariance $C_d$. $C_d$ and $C_t$ are matrixes and d, m and $d_t$ are vectors. When $d_t$=0 and $C_t$=0, the equation becomes equation (4) as earlier described.

Accordingly, the method further comprises:

obtaining a noise model for the PET image, and obtaining a forward operator g, for example in form of a linear point spread function operator $G_{PSF}$ obtaining a modelling error due to using a finite size lookup table, and using the modelling error, preferable before using, for each subset-image $d_{ss}$ from the PET image, an extended rejection sampler to sample the posterior distribution based on the lookup table.

Accordingly, The modelling error is included in the calculation of the likelihood L(m).

The modelling error is found by making a sample of a probability density representing the modelling error. The sample representing the modelling error obtained by comparing by examining a new, smaller, set of realizations from the prior, for instance, 1000, sets of data.

Each model-image in the modelling error sample is called an error-model-image m'. The error-model-images m' from the modelling error sample is placed in a modelling-error-table. From error-model-image m', an error-data-image d' is calculated using the function g. So each set of data in the modelling-error-table comprises an error-model-image m' and an error-data-image d' corresponding to m* and d* in the original lookup table.

Now for each set of data in the modelling-error-table, the error-model-image m' is compared to the model-image m* from all the sets of data in the original lookup table, and the model-image m* from the lookup table that is most similar to the error-model-image m' in the modelling-error-table is selected.

To determine which model-image m* is most similar to the error-model-image m' can be done by for each set of data in the lookup table to subtract the model-image m* from the error-model-image m' and sum the elements in the result, and then select the set of data with the lowest sum. m* and m' are vectors of pixel tracer intensities, so it is a simple vector subtraction and then a summation of all the elements in the resulting vector.

Then the distance between the data-image d* from the lookup table and the error-data-image d' from the error model can be calculated. d* and d' is also implemented as vectors, so this is simple vector subtractions.

For each set of data in the modelling-error-table, the most similar set of data from the lookup table is selected and the data-image d* selected from the set of data from the lookup table and saved in the modelling-error-table as $d_{app}$, and all the distances are calculated and a matrix DD* is created with all the distances.

$$DD^* = [d'_1 - d_{app1}, d'_2 - d_{app2}, \ldots d'_{Ne} - d_{appNe}]$$

DD* is then an $N_M \times N_e$ size matrix, where $N_M$ is the number of pixels represented in a data-image and $N_e$ is the number of sets of data in the modelling-error-table. The mean $d_t$ (of size $N_M \times 1$) and covariance $C_t$ (of size $N_M \times N_e$) can easily be computed from DD* such that the modelling error can be described by a Gaussian probability density function with mean $d_t$ and covariance $C_t$.

Further details for how to find the modelling error with mean $d_t$ and covariance $C_t$ and the equation for L(m) is described in the reference:

Hansen, T. M., Cordua, K. S., Jacobsen, B. H., & Mosegaard, K. (2014). Accounting for imperfect forward modelling in geophysical inverse problems—Exemplified for cross-hole tomography. Geophysics, 79(3), H1-H2

The modelling error is computed, however, for very large training sets, the modelling error will be negligible, and there is no need to compute the modelling error. Also, in case the magnitude of the measurement error is much higher than the modelling error (comparing $C_d$ and $C_t$), then one can also ignore modelling errors. If the differences are small for all the sets of data in the error model, there is no problem. Then the modelling error is insignificant.

Output Representation Images

When all the posterior distributions for all the subset-images $d_{ss}$ has been accepted, then the posterior distributions are used to determine output representation images of the data.

Accordingly, determining a representation image comprises calculating a pixel-wise mean of the model-images m in the posterior distribution, and outputting the pixel-wise mean of the posterior distribution as the representation image.

The representation images can simply be created by calculating mean intensities for all the pixels in the model-images m in the posterior distribution, and output an image based on these mean intensities. Alternatively, a representation image can be determined by finding the most likely pixel intensity for each pixel.

Accordingly, determining a representation image comprises determining the most likely pixel intensity for pixels of a representation image based on pixels intensities for the model-images m in of the posterior distribution, and wherein the representation image is based on the most likely pixel intensity.

The representation images can also be created by counting the number of pixels with a high pixel intensity, that is high tracer intensity, for example, pixels with a tracer intensity higher than 15000. The percentage of the pixels with a high tracer intensity is calculated and the result is a probability that the pixel intensity is higher than 15000. Then pixel with a high probability is black in the representation image, while pixels with a low probability is white and all between is in grayscale.

Accordingly, determining a representation image comprises determining the probability of pixels with a pixel intensity higher than a selected intensity for a representation image based on pixel intensities for the model-images m in the posterior distribution, and wherein the representation image is based on probability of pixels with a pixel intensity higher than a selected intensity.

Obviously, the representation image can be determined in many different ways by using many different statistical calculation methods.

To improve the quality of a representation image choosing only the centre pixel intensity form the model-images in the posterior distribution can be advantageous.

When the subset-image is selected, not only a single pixel is chosen, but a group of pixels. This is because using $G_{PSF}$ the pixel intensity for a single pixel is dependent on the intensity and noise of the neighbour pixels, therefore some rows of neighbour pixels are needed for getting the right result for the single pixel. Therefore, a method to make a representation image is to make subset-images $d_{ss}$ by moving the frame around the subset-image $d_{ss}$ only one pixel at a time, making a subset-image $d_{ss}$ for each pixel in the PET image, so the subset-image $d_{ss}$, for instance, can be 9×9 pixels. The centre pixel is surrounded by the neighbour pixels in the subset-image $d_{ss}$, but when the posterior distribution accepted for the subset-image $d_{ss}$, is analyzed only the intensity of the centre-pixel is used for the representation image and the other 80 pixels around the centre pixel is ignored.

For a subset-image of 9×9 pixels, the calculation gives the correct centre pixel value in the given case. Using a larger subset-image, more of the centre pixel can be used, and hence potentially lead to increased efficiency. Increased efficiency will depend on the increased computational demands to set up and evaluate the lookup-table for a larger subset-image. For example, in a similar way, the centre 2×2, 3×3, 4×4 pixels in the posterior distribution images for a given subset-image $d_{ss}$ can be used for analysis and the remaining outer pixel be ignored.

Accordingly, only the centre pixel intensity, or a group of centre pixels intensities, for the model-images m in the posterior distribution is used for generating the representation image.

The invention relates to a computer program product comprising at least one computer having data storage means in connection therewith, and the computer program comprising instructions which, when the program is executed by a computer, cause the computer to carry out the steps of the method of the image reconstruction.

Accordingly, the invention relates to a medical imaging device comprising a processor, wherein the processor is configured to:

obtain a lookup table of pre-computed sets of data, each pre-computed set of data comprises a model-image m* from a sample M* and a corresponding data-image d*, the model-image m* is a realization from a prior $\rho(m)$, the prior $\rho(m)$ is a statistical model based on expert data, each model-image m* is a representation of an image of one, or more, pixels, the data-image d* is determined based on the model-image m* in the same set of data, each data-image d* is a representation of one, or more, pixels, obtain a PET image and dividing the PET image into subset-images $d_{ss}$, each subset-image $d_{ss}$ is a representation of one or more pixels, using, for each subset-image $d_{ss}$ from the PET image, an extended rejection sampler to accept model-images m* from the lookup table representing the posterior distribution given the subset-image $d_{ss}$, and determining and outputting a representation image based on the sample of the posterior distribution.

In an aspect of the invention, the invention relates to a computer program product being adapted to enable a computer system comprising at least one computer having data storage means in connection therewith to control a medical image device, such as a computer program product comprising instructions which, when the program is executed by a computer, cause the computer to carry out the method of the invention.

This aspect of the invention is particularly, but not exclusively, advantageous in that the present invention may be accomplished by a computer program product enabling a computer system to carry out the operations of the method of the image reconstruction of the invention when down- or uploaded into the computer system. Such a computer program product may be provided on any kind of computer-readable medium, or through a network.

The individual aspects of the present invention may each be combined with any of the other aspects. These and other aspects of the invention will be apparent from the following description with reference to the described embodiments.

BRIEF DESCRIPTION OF THE FIGURES

The method according to the invention will now be described in more detail with regard to the accompanying figures. The figures show one way of implementing the present invention and is not to be construed as being limiting to other possible embodiments falling within the scope of the attached claim set.

The figures show one way of implementing the present invention and is not to be construed as being limiting to other possible embodiments falling within the scope of the attached claim set.

DETAILED DESCRIPTION OF AN EMBODIMENT

Figure 1:
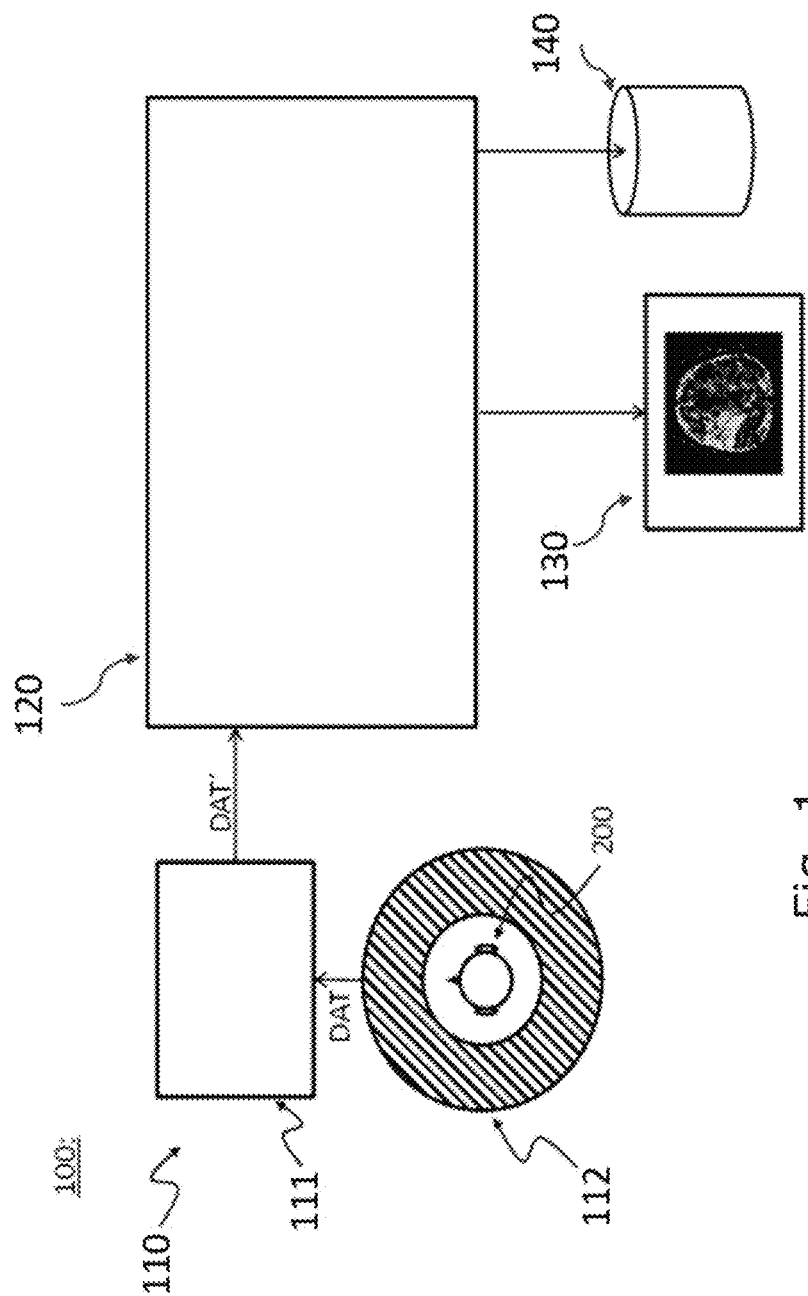
FIG. 1 shows a schematic drawing of a medical imaging system.

FIG. 1 is a schematic drawing of a medical imaging system 100 in an aspect of the present invention. The system 100 comprises a scanning system 110, capable of obtaining data representative of a contrast agent concentration as a function of time of an injected contrast agent into a human 200, whose head is schematically seen in a cross-sectional view. One or more parts of the human can be imaged, e.g. the brain. The system comprises a PET scanner 112 and a corresponding measurement and control system 111. The scanner obtains primary data DAT which are communicated to the measurement and control system 111, where further processing resulting in secondary data DAT' being communicated to a processor 120.

In the processor 120, a method for estimating perfusion indices for the human 200 is implemented using the obtained data DAT and DAT' representative of a contrast agent concentration as a function of time of an injected contrast agent.

The processor may be operably connected to a display device 130, such as a computer screen or a monitor, to enable showing an image of the resulting PET image as schematically indicated. Alternatively, or additionally, the PET image may be communicated to a storage device 140 of any suitable kind for later analysis and diagnostic purposes.

Figure 2A:
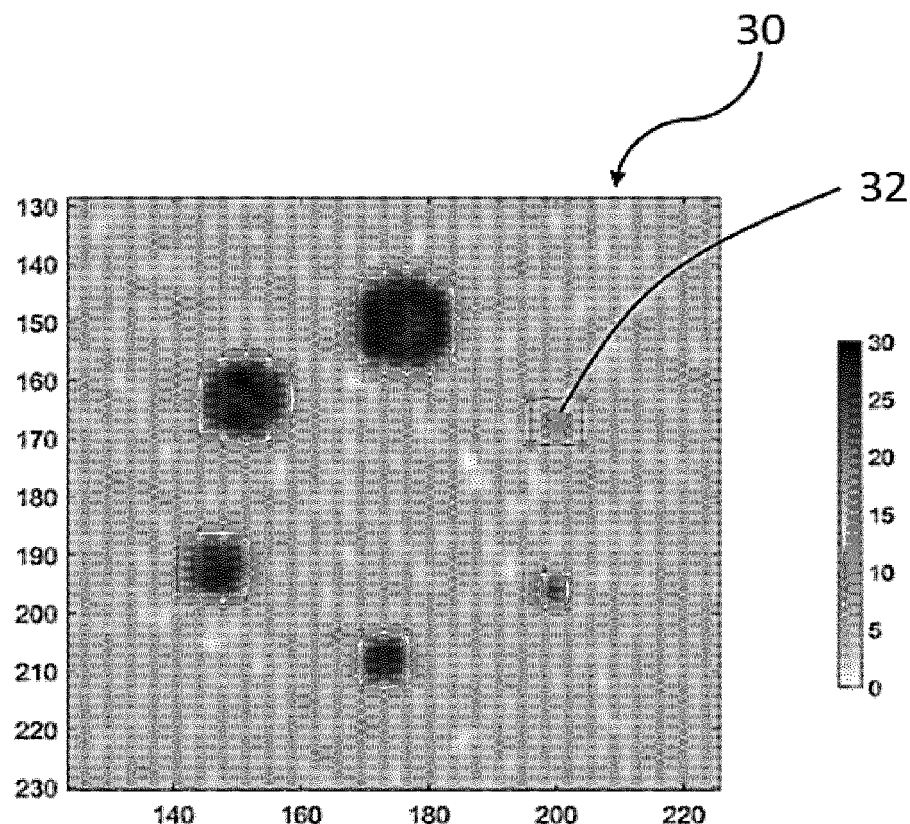
FIGS. 2a and 2b show a 2D observed PET image and a subset-image from the PET image.
Figure 2B:
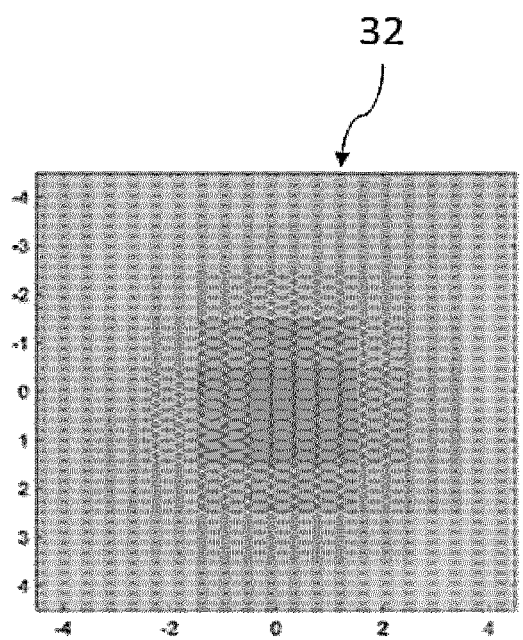

FIG. 2a shows a 2D PET image, as output from a PET scanner. The 2D PET image is an example of a PET image 30. On FIG. 2b one subset-images $d_{ss}$ 32 is shown in a marked square where each tracer intensity of the subset-images $d_{ss}$ 32 is shown as a pixel representing the tracer intensity. This subset-image $d_{ss}$ 32 representation has 9×9 pixels.

Figure 3:
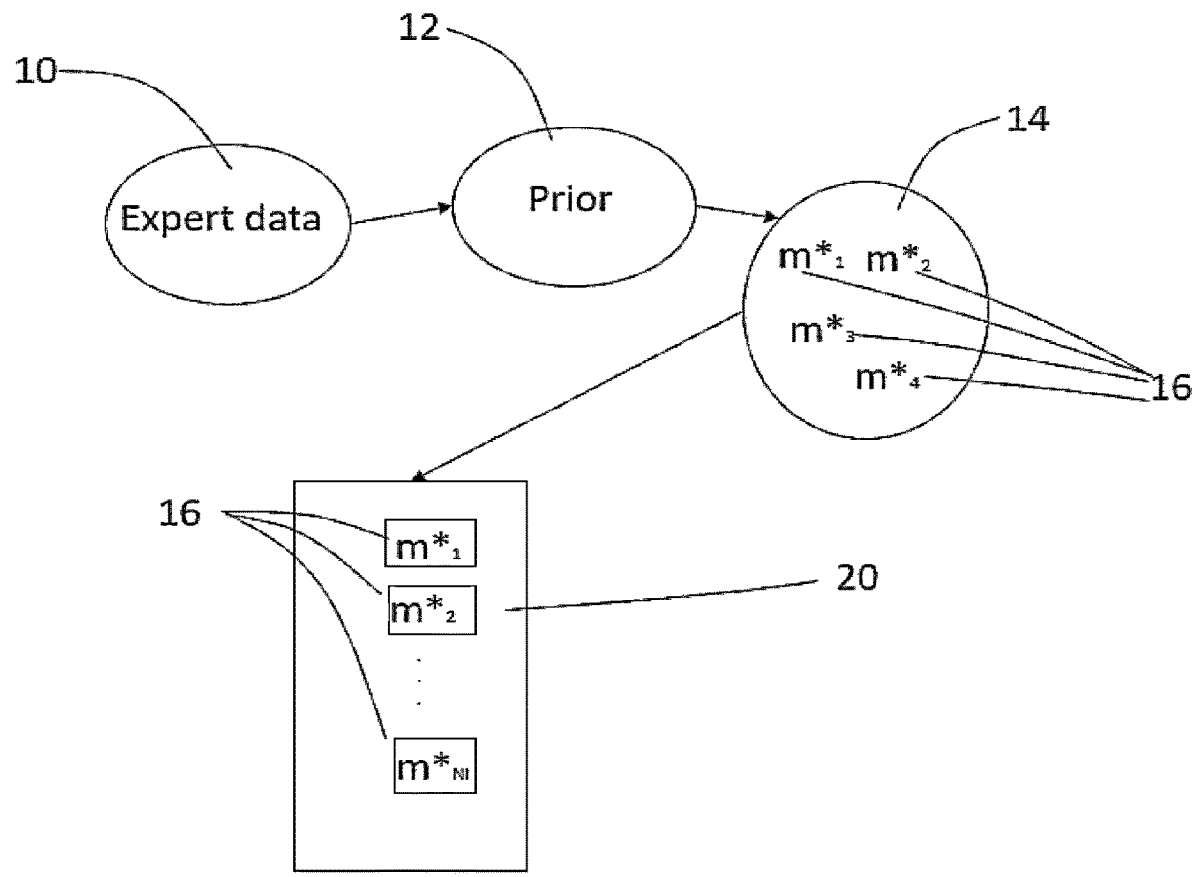
FIG. 3 shows that expert data is used to generate the prior $\rho(m)$, and the prior $\rho(m)$ is used to make realizations for the sample M*, which then is placed in the lookup table.

FIG. 3 shows that the prior $\rho(m)$ 12 is generated based on expert data 10, the sample M* 14 is created from the prior $\rho(m)$ 12 containing model-images m* 16 which is realizations from the prior $\rho(m)$ 12. The model-images m* 16 is then placed in a look-up table 20.

Figure 4:
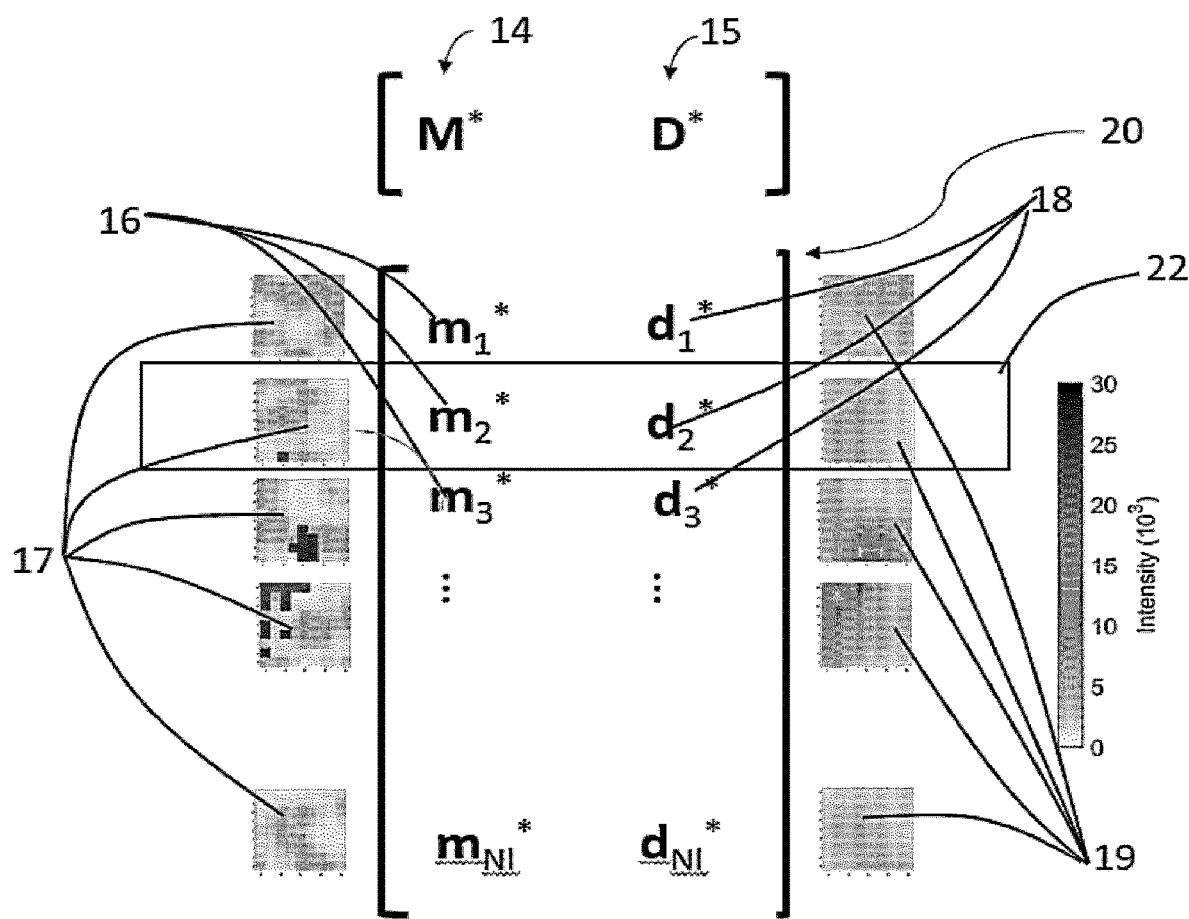
FIG. 4 shows an overview of the lookup table.

FIG. 4 is a diagram displaying the lookup table 20 with the sample M* 14. The sample M* includes $N_l$ model-images m* 16. Each model-image m* 16 represents at least 1 pixel but can have 10, 100, 1000 pixels or any suitable number of pixels. All model-images m* 16 represents the same number of pixels. Each model-image m* 16 in the sample M* 14 is placed in a lookup table 20 in a first column.

For each model-image m* 16 a function g is applied to generate a data-image d* 18. The data-image d* 18 is placed in a second column D* 15 in the lookup table.

That is, the lookup table 20 has two columns M* 14 and D* 15 and it has $N_l$ rows. Each row is a set of data 22 comprising a model-image m* 16 in a first column and a data-image d* 18 in a second column.

The left side of FIG. 4 shows of the model-images m* 16 from the sample M* 14 from the lookup table 20 represented as an image 17 wherein each intensity pixel value from m* 16 is represented by a greyscale colour.

The right side of FIG. 4 shows the data-images d* 18 from the lookup table 20 represented as an image 19 wherein each intensity pixel value from d* 18 is represented by a greyscale colour.

Figure 5:
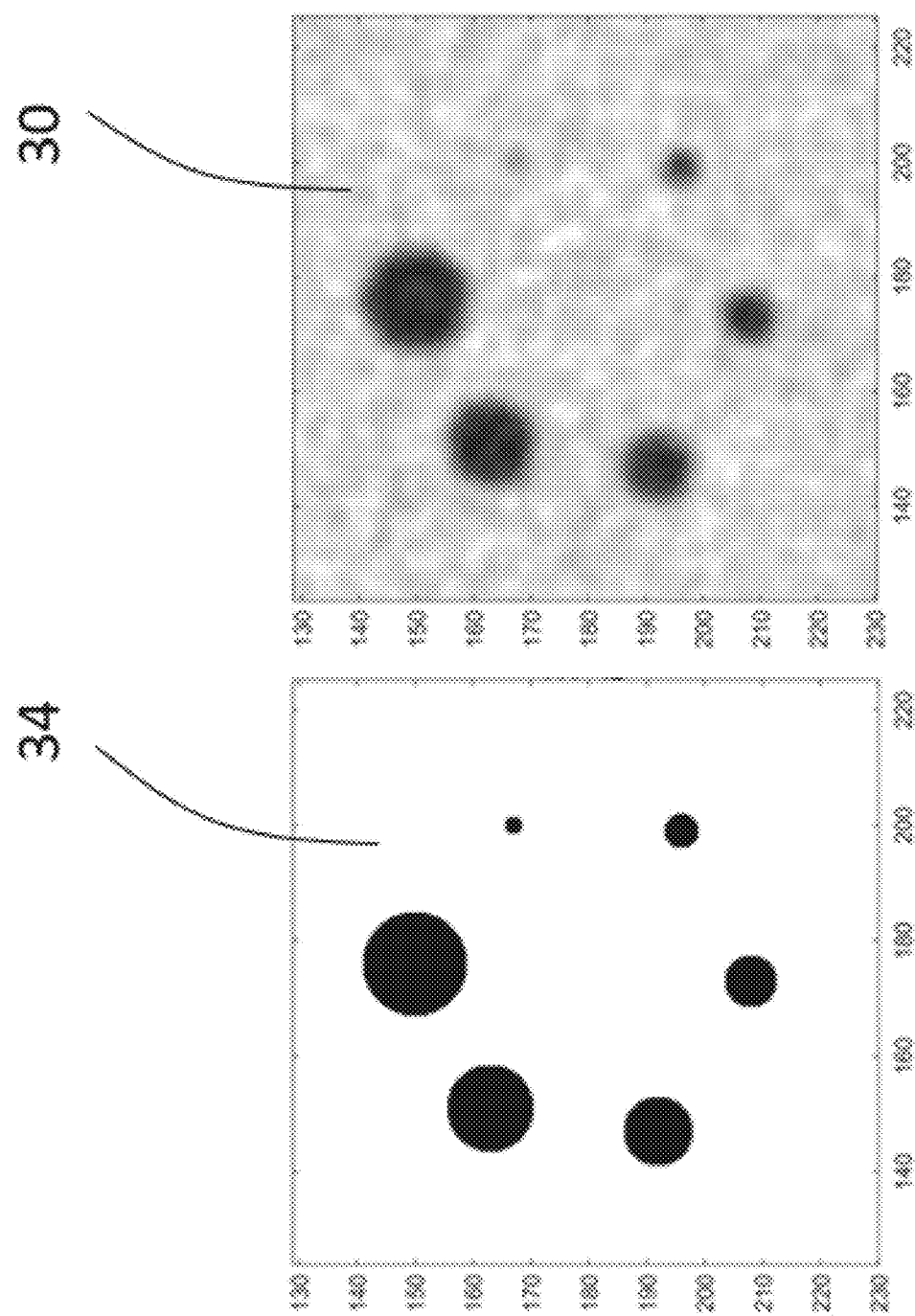
FIG. 5 shows an example of simulating the forward process (Eqn. 5) from a known target (left) to an example of the resulting PET image.

The image 34 in FIG. 5 is the representation image resulting from applying the forward method, the method of the invention, to the PET image (30).

Figure 6:
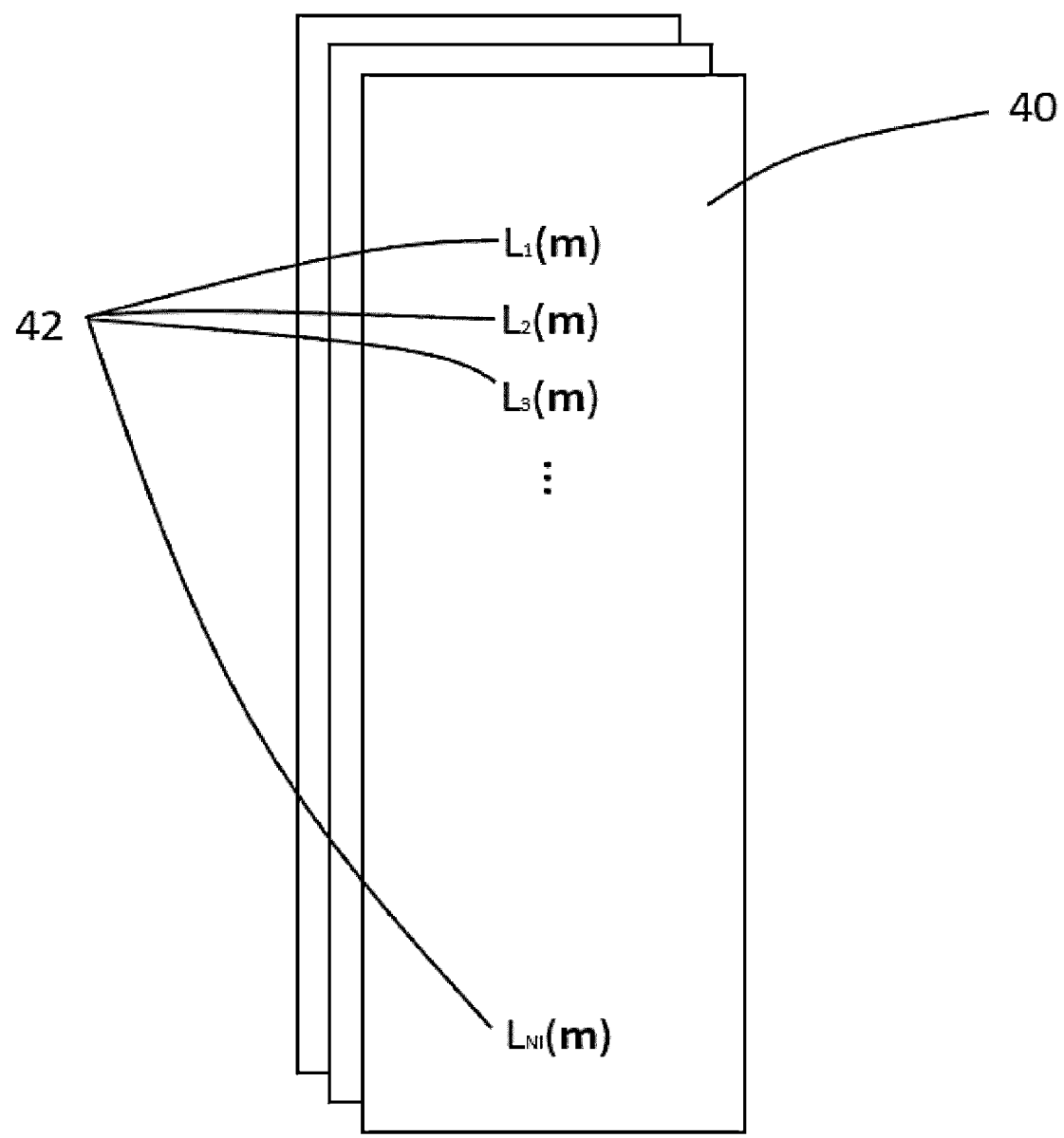
FIG. 6 shows the likelihoods for subset-images.

FIG. 6 illustrates that for each subset-image $d_{ss}$ 32 from the PET image 30, a likelihood L(m) 42 is calculated for each set of data 22 in the lookup table 20. In FIG. 6 a list 40 of likelihoods L(m) 42 for a subset-image $d_{ss}$ 32 is shown, and it is also illustrated that different lists 40 are made for each subset-image $d_{ss}$ 32. This is only one example of a possible implementation, of course in the computer program implementation of the method the calculation and storage of the likelihoods L(m) 42 can be implemented in many different ways.

Figure 7:
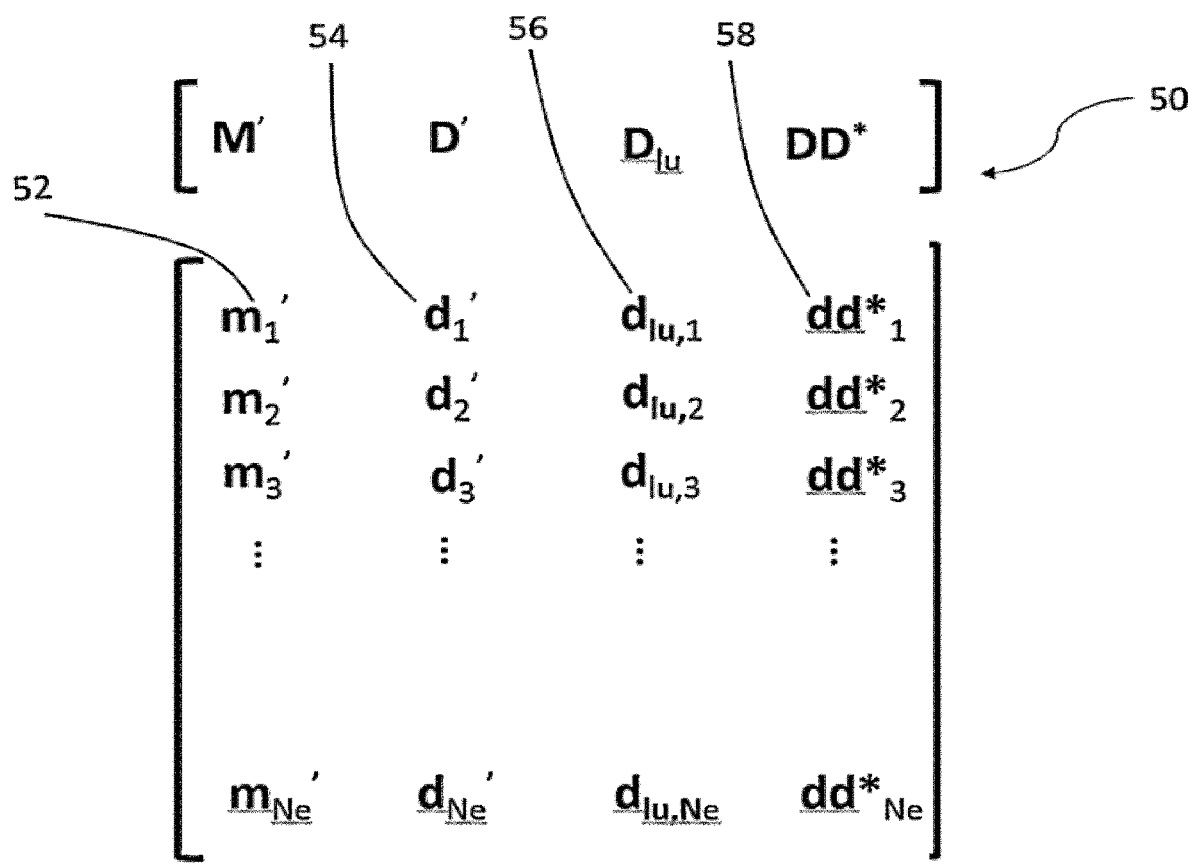
FIG. 7 shows a table illustrating the modelling-error-table.

In FIG. 7 the modelling error calculation is illustrated. If there is a modelling error, then to calculate the Likelihood L(m) the modelling error must be known. To calculate the Likelihood L(m) a modelling-error-table 50 is created. FIG. 7 shows the modelling-error-table 50 with $N_e$ sets of data. Each set of data comprises an error-model-image m' 52. The modelling-error-table 50 is similar to the lookup table 20 based on the prior ρ(m). But the modelling-error-table 50 typically require fewer sets of data, for instance 1000.

From the error-model-image m' 52 an error-data-image d' 54 is calculated using the function g. Each error-model-image m' 52 is compared to all model-images m* 16 in the lookup table 20 to find the most similar set of data in the look-up table 20. When the most similar set of data is found, the data-image d* 18 for the chosen set of data is taken and placed in the modelling-error-table 50 as the data-image $d_{lu}$ 56. Then the distance between d' 54 and $d_{lu}$ 56 is calculated and the result dd* 58 is placed in the modelling-error-table 50 in a column DD*. The mean $d_t$ and the covariance $C_t$ is now computed from the column DD*.

Figure 8:
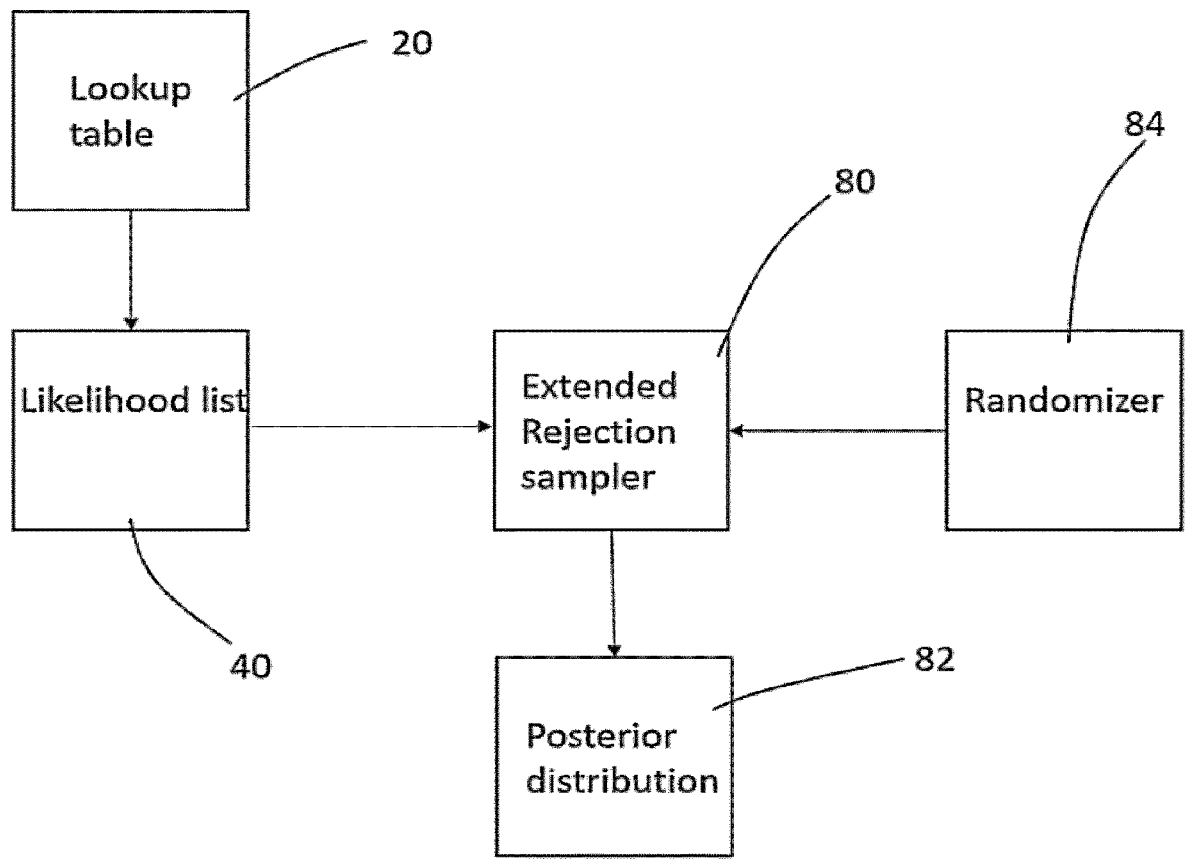
FIG. 8 is a diagram illustrating the dataflow including the extended rejection sampler.

FIG. 8 shows that based on the likelihood L(m) in the list 40 for a given subset-image $d_{ss}$, the extended rejection sampler 80 selects a posterior distribution 82 from the lookup table 20. This is done for each subset-image $d_{ss}$. The selection is done by calculating $P_{acc}$ and comparing $P_{acc}$ with a number from a randomizer 84. A new randomized number is generated for each comparison made.

The comparison starts from the top of the list 40 with calculating $P_{acc}$ based on the likelihood $L_1(m)$ and generating a random number between 0 and 1. If the random number is larger than $P_{acc}$, then the set of data 22 from the lookup table 20 is rejected, but if the random number is smaller than $P_{acc}$, then the corresponding set of data 22 from the lookup table 20 is accepted for the posterior distribution 82 for the given subset-image $d_{ss}$ and the model-image m* 16 from the set of data 22 in the lookup table 20 is added to the posterior distribution 82. Then the selection continues by calculating $P_{acc}$ for $L_2(m)$ and so on until the requested number of sets of data 22 from the lookup table 20 has been accepted and the model-image m* 16 added to the posterior distribution 82. If all the rows in the list 40 has been tested without reaching the requested number, the selecting starts again from the top of the subset-image list 40 and testing again the rows that was not selected in the first run and so on until the requested number of model-images m* has been added to the posterior distribution 82.

Figure 9:
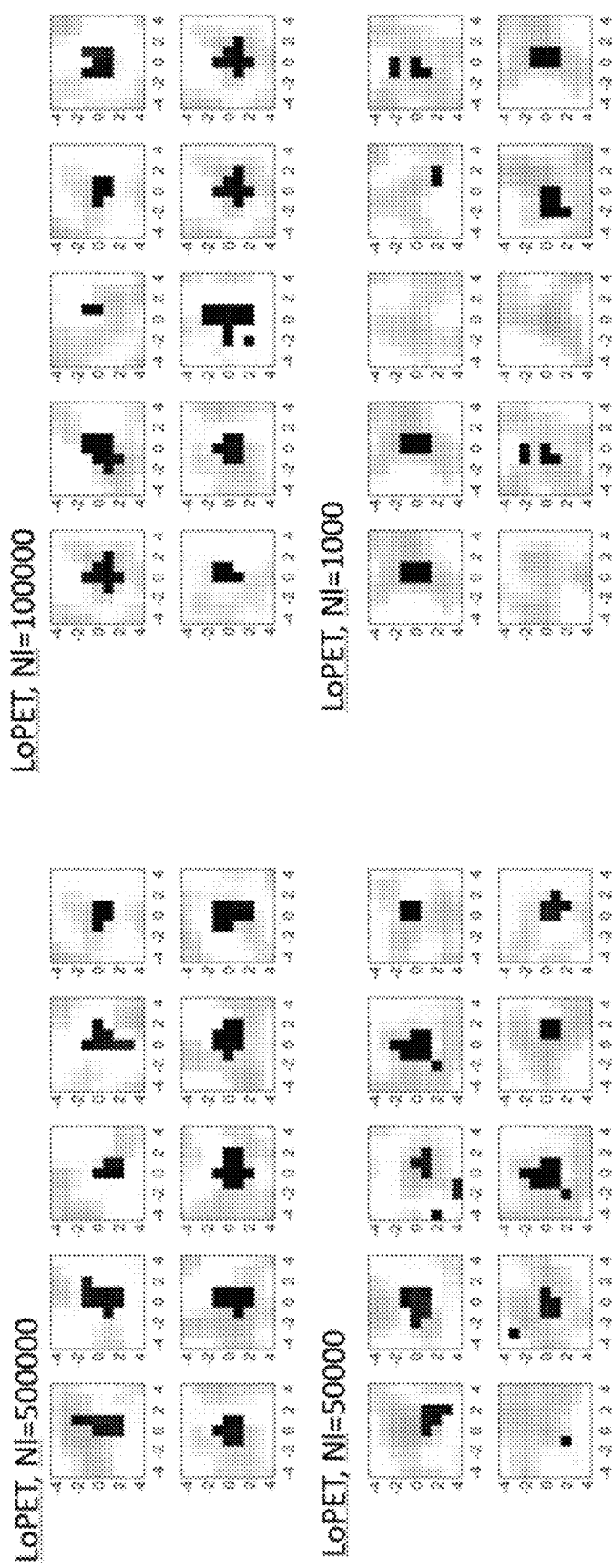
FIG. 9 shows selections of images from a posterior distribution, for different sizes of lookup tables.

FIG. 9 shows 10 image representations 17 of model-images m* 16 selected by the extended rejection sampler 80 for the posterior distribution 82 from lookup tables of different sizes, 1000, 50000, 100000 and 500000 respectively.

Figure 10:
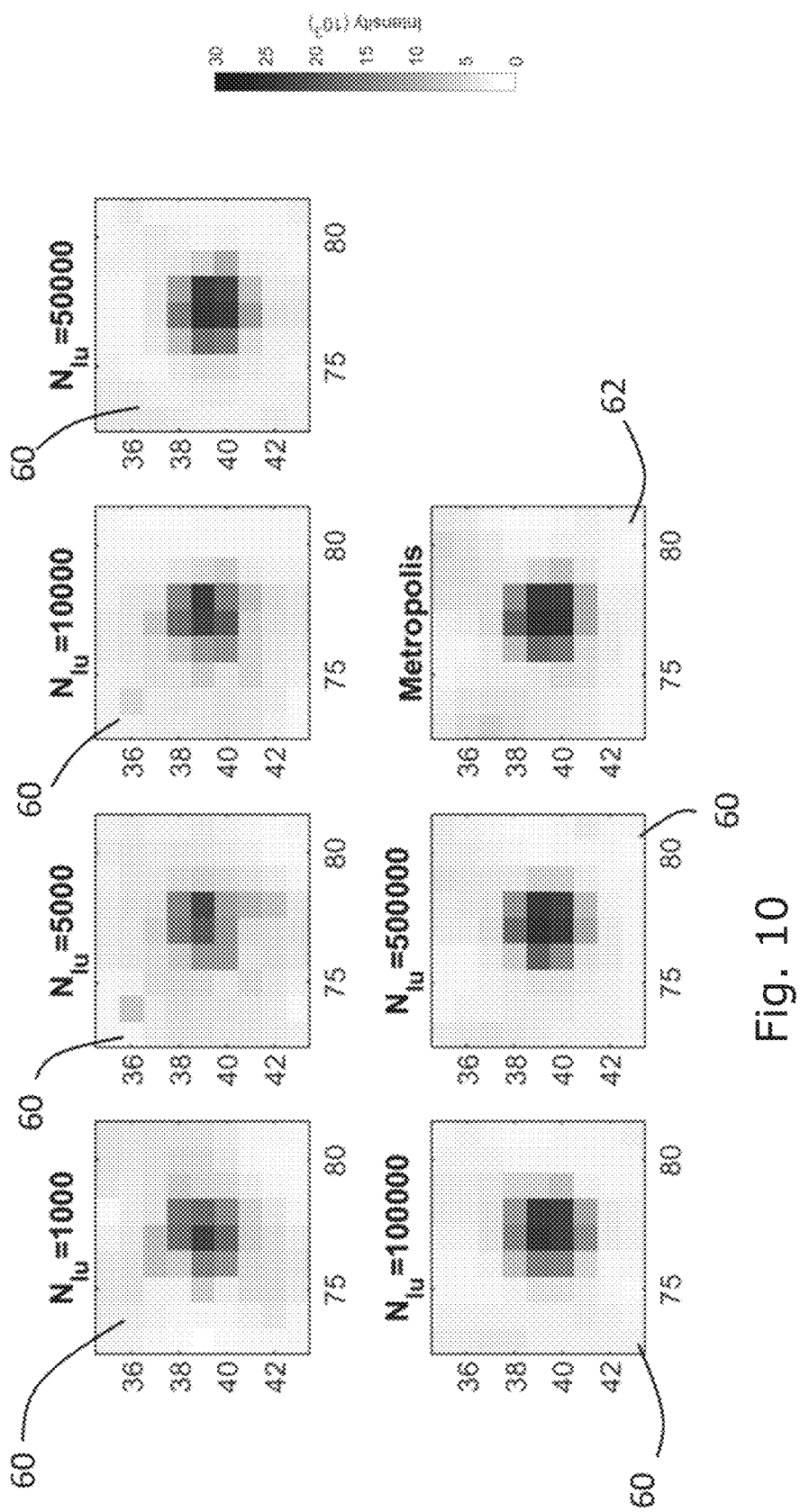
FIG. 10 shows an example of a pointwise mean intensity for the model-images in a posterior distribution for a representation image.

FIG. 10 shows six representation images 60 as a pointwise mean estimate of the intensity for the model-images m* in a posterior distribution 82 of with representations of ten model-images m* are shown in FIG. 9. The six representation images are created using lookup tables of the sizes of 1000, 5000, 10000, 50000, 100000 and 500000 sets of data respectively. Further, an image 62 made by a prior art method, ProPET, used in WO2018/215357, is shown for comparison, showing that using an extended rejection sampler with a lookup table with 500000 sets of data gives the same result as using the prior art ProPET method.

Figure 11:
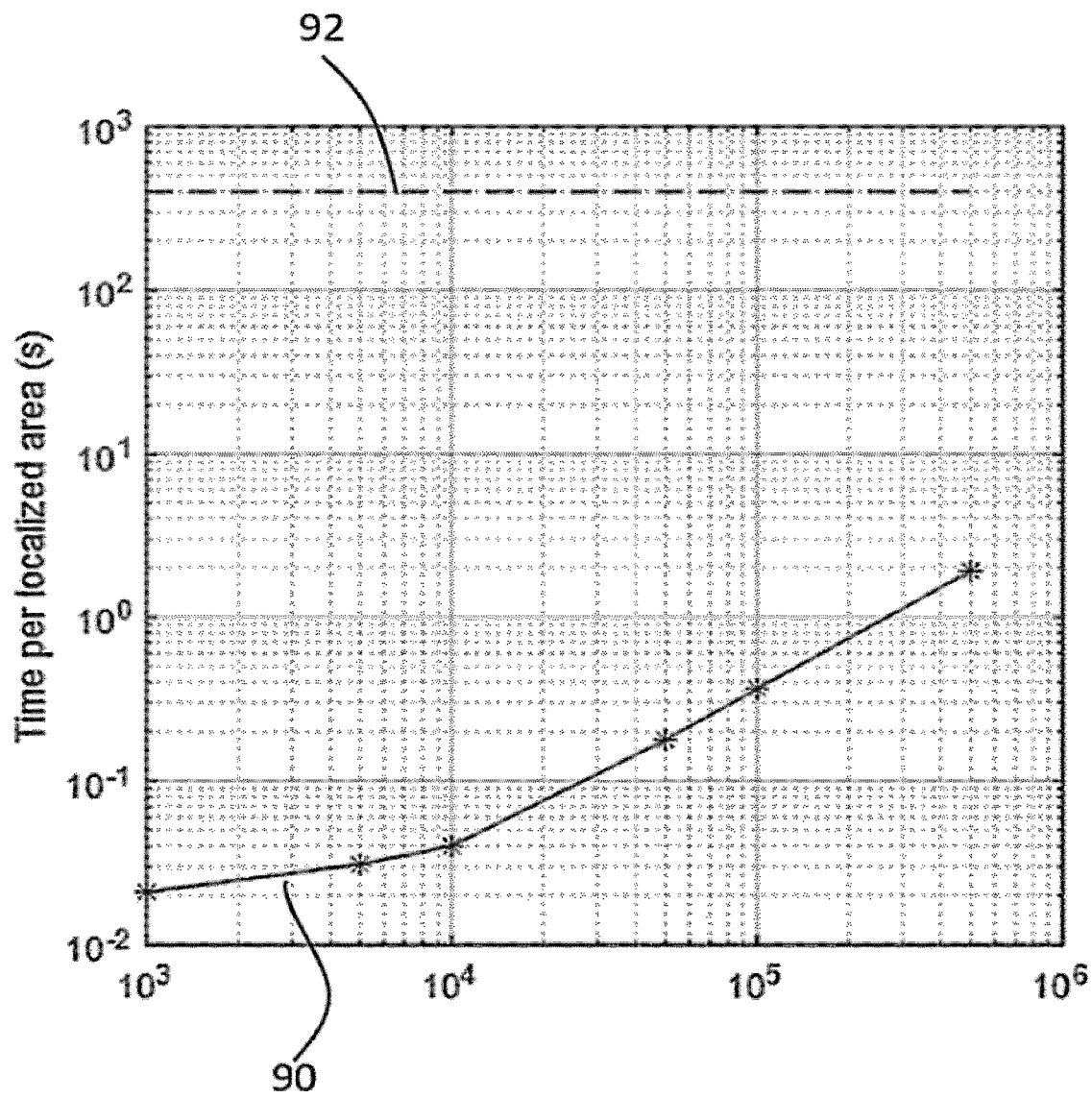
FIG. 11 shows CPU time needed for calculating for the LoPET method compared to a prior art method.

FIG. 11 shows the CPU time per subset-image analysed by LoPET, the method of the invention and for the prior art method ProPET as shown in FIG. 10. Graph with reference no. 90 shows the CPU time for the LoPET method and graph with reference no. 92 shows the CPU time used by the prior art method ProPET. It can be seen that the CPU time is considerably lower for LoPET than for ProPET, so LoPET, the method of the invention is considerably faster than the prior art method ProPET.

Figure 12:
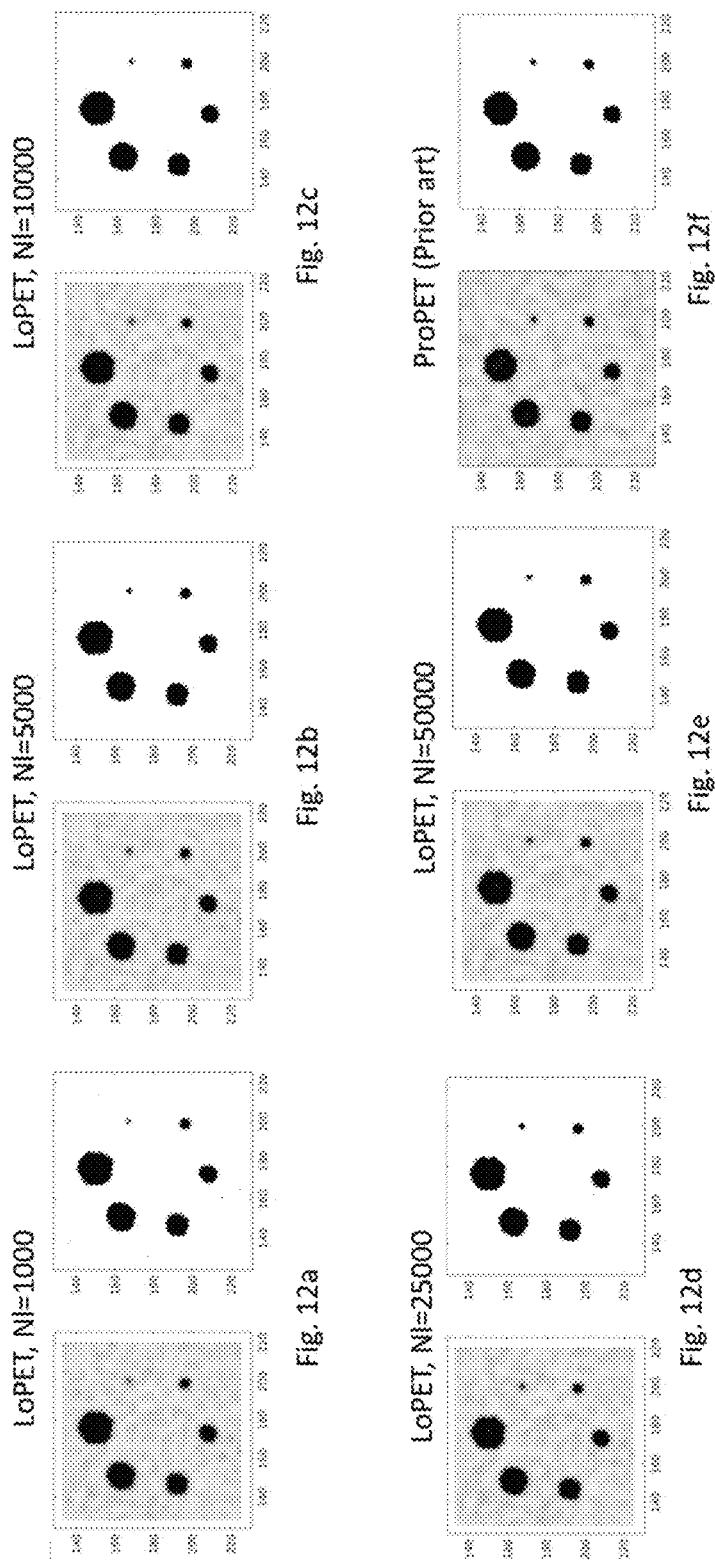
FIG. 12 shows representation images for LoPET compared to the prior art method.

FIG. 12 shows representation images of the output using the extended rejection sampler with lookup tables.

FIG. 12a shows representation images for the method of the invention using a lookup table with 1000 sets of data. FIG. 12b shows representation images for the method of the invention using a lookup table with 5000 sets of data. FIG. 12c shows representation images for the method of the invention using a lookup table with 10000 sets of data. FIG. 12d shows representation images for the method of the invention using a lookup table with 25000 sets of data. FIG. 12e shows representation images for the method of the invention using a lookup table with 50000 sets of data. FIG. 12f shows representation images based on the prior art ProPET method.

In all the FIGS. 12a-12f to the left is an representation image based on the mean intensity for all the pixels in the posterior distribution and to the right an representation image made by for each pixel to count the number of pixels in the posterior distribution with a tracer intensity larger than 15000. This gives a probability between 0 and 1 for that this pixel has a tracer intensity larger than 15000 and this probability is plotted in the colour intensity in FIG. 12c. If the probability that the tracer intensity is larger than 15000 is 1.00, the pixel is black, if it is 0.00 it is white and all the other probability values is grayscale.

Comparing the figures it is clear that even for small sizes of the lookup table similar quality of the representation images is achieves as in the prior art method, with the method of the invention being considerable faster than the prior art method.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims may possibly be advantageously combined, and the mentioning of these features in different claims does not exclude that a combination of features is not possible and advantageous.

In other embodiments, the present invention also relates to:

1. A computer-implemented method for image reconstruction for medical imaging of a subject, the method comprising:
   obtaining a lookup table (20) of pre-computed sets of data (22), each pre-computed set of data (22) comprises a model-image m* (16) from a sample M* (14) and a corresponding data-image d* (18), each model-image m* (16) is a representation of an image of one, or more, pixels,
   obtaining a PET image (30) and dividing the PET image (30) into subset-images $d_{ss}$ (32) each subset-image $d_{ss}$ (32) is a representation of one, or more, pixels,
   using for each subset-image $d_{ss}$ (32) from the PET image (30) an extended rejection sampler (80) to accept model-images m* (16) from the lookup table (20) representing the posterior distribution (82) given the subset-image $d_{ss}$ (32), and
   determining and outputting a representation image (94) based on the sample of the posterior distribution (82).

2. The computer-implemented method for image reconstruction according to embodiment 1, wherein each pre-computed set of data (22) in the lookup table (20) comprises a model-image m* (16) which is a realization from a prior ρ(m) (12), the prior ρ(m) (12) is a statistical model based on expert data.

3. The computer-implemented method for image reconstruction according to embodiment 1 or 2, wherein each pre-computed set of data (22) in the lookup table (20) comprises a data-image d* (18) determined based on the model-image m* (16) in the same set of data (22), each data-image d* (18) is a representation of one, or more, pixels.

4. The computer-implemented method for image reconstruction according to embodiment 1-3, wherein the method further comprises that for each subset-image $d_{ss}$ (32), a likelihood L(m) (42) is calculated for each pre-computed set of data (22) in the lookup table (20).

5. The computer-implemented method for image reconstruction according to any of the preceding embodiments, wherein the method further comprises that for each subset-image $d_{ss}$ (32), a probability acceptance $P_{acc}$ is calculated for each pre-computed set of data (22) in the lookup table (20) for the given subset-image $d_{ss}$ (32), based on the likelihood L(m) (42) for this pre-computed set of data (22) for the given subset-image $d_{ss}$ (32) divided by a maximum likelihood max(L) for the given subset-image $d_{ss}$ (32).

6. The computer-implemented method for image reconstruction according to any of the preceding embodiments, wherein the method further comprises for each subset-image $d_{ss}$ (32) that the probability acceptance $P_{acc}$, calculated for each pre-computed set of data (22) in the lookup table (20) for the given subset-image $d_{ss}$, is used by the extended rejection sampler (80) to determine, whether to accept the model-image m* from the pre-computed set of data (22) in the lookup table (20) for a posterior distribution (82) for the given subset-image $d_{ss}$.

7. The computer-implemented method for image reconstruction according to any of the preceding embodiments, wherein a random value is generated for each pre-computed set of data (22) in the lookup table (20) to compare with the probability acceptance $P_{acc}$ to decide whether to accept the model-image m* from the pre-computed set of data (22) in the lookup table (20) for the posterior distribution (82).

8. The computer-implemented method for image reconstruction according to any of the preceding embodiments, wherein the method further comprises:
   obtaining a noise model for the PET image (30), and
   obtaining a forward operator g, for example in form of a linear point spread function operator $G_{PSF}$
   obtaining a modelling error due to using a finite size lookup table (20), and
   using the modelling error, preferable before using, for each subset-image $d_{ss}$ from the PET image (30), an extended rejection sampler (80) to sample the posterior distributions (82) based on the lookup table (20).

9. The computer-implemented method for image reconstruction according to embodiments 8, wherein the modelling error is included in the calculation of the likelihood L(m).

10. The computer-implemented method for image reconstruction according to any of the preceding embodiments, wherein determining a representation image (94) comprises calculating a pixel-wise mean of the model-images m (16) of the posterior distribution (82) and outputting the pixel-wise mean of the posterior distribution (82) as the representation image (94).

11. The computer-implemented method for image reconstruction according to any of the preceding embodiments, wherein determining a representation image (94) comprises determining the most likely pixel intensity for pixels of a representation image (94) based on the pixel intensities for the model-images m (16) in the posterior distribution (82), and wherein the representation image (94) is based on the most likely pixel intensities.

12. The computer-implemented method for image reconstruction according to any of the preceding embodiments, wherein determining a representation image (94) comprises determining the probability of pixels with a pixel intensity higher than a selected intensity for a representation image (94) based on pixel intensities for the model-images m (16) in the posterior distribution (82), and wherein the representation image (94) is based on probability of pixels with a pixel intensity higher than a selected intensity.

13. The computer-implemented method for image reconstruction according to any of the preceding embodiments, wherein only the centre pixel intensity, or a group of centre pixels intensities, for the model-images m (16) in the posterior distribution (82) is used for generating the representation image (94).

14. A medical imaging device comprising a processor, wherein the processor is configured to:
obtain a lookup table (20) of pre-computed sets of data (22), each pre-computed set of data (22) comprises a model-image m* (16) from a sample M* (14) and a corresponding data-image d* (18), each model-image m* (16) is a representation of an image of one, or more, pixels,
obtain a PET image (30) and dividing the PET image (30) into subset-images $d_{ss}$ (32), each subset-image $d_{ss}$ (32) is a representation of one or more pixels,
using, for each subset-image $d_{ss}$ (32) from the PET image (30), an extended rejection sampler (80) to accept model-images m* (16) from the lookup table (20) representing the posterior distribution (82) given the subset-image $d_{ss}$ (32), and
determining and outputting a representation image (94) based on the sample of the posterior distribution (82).

15. A computer program software being adapted to enable a computer system comprising at least one computer having data storage means in connection therewith to control a medical image device according to embodiments 14, such as a computer program product comprising instructions which, when the program is executed by a computer, cause the computer to carry out the method according to any of the embodiments 1-13.

REFERENCES

Tarantola, A., & Valette, B. (1982). Inverse problems=quest for information. Journal of geophysics, 50(1), 159-170.
Metropolis, Nicholas, et al. "Equation of state calculations by fast computing machines." The journal of chemical physics 21.6 (1953): 1087-1092.
Hansen, T. M., Cordua, K. S., Jacobsen, B. H., & Mosegaard, K. (2014). Accounting for imperfect forward modeling in geophysical inverse problems-exemplified for crosshole tomography. Geophysics, 79(3), H1-H21
Hansen, Thomas Mejer, et al. "Probabilistic integration of geo-information." Integrated imaging of the earth: Theory and applications 218 (2016): 93-116.
Deutsch, C. V., & Journal, A. G. (1992). Geostatistical software library and user's guide. New York, 119(147).
Mariethoz, G., & Caers, J. (2014). Multiple-point geostatistics: stochastic modeling with training images. John Wiley & Sons.
Mosegaard, Klaus, and Albert Tarantola. "Monte Carlo sampling of solutions to inverse problems." Journal of Geophysical Research: Solid Earth 100.B7 (1995): 12431-12447.

The above-listed references are hereby incorporated by reference in their entirety.

The invention claimed is:

1. A computer-implemented method for image reconstruction for detecting a tumor in medical imaging of a subject, the method comprising:
constructing a lookup table of pre-computed sets of data based in part on image data comprising at least one of: tumors, metastases, or a cell structure associated with tumor growth;
storing the lookup table;
obtaining the lookup table of pre-computed sets of data, each pre-computed set of data comprises a model-image m* from a sample M* and a corresponding data-image d*, the model-image m* is a realization from a prior ρ(m), the prior ρ(m) is a statistical model based on expert data, each model-image m* is a representation of an image of one, or more, pixels, the data-image d* is determined based on the model-image m* in the same set of data, each data-image d* is a representation of one, or more, pixels,
obtaining a PET image and dividing the PET image into subset-images $d_{ss}$ each subset-image $d_{ss}$ is a representation of one or more pixels,
using for each subset-image $d_{ss}$ from the PET image an extended rejection sampler to accept model-images m* from the lookup table representing a posterior distribution given the subset-image $d_{ss}$, wherein using the extended rejection sampler comprises computing a likelihood function for all m* accepted from the lookup table, and accepting them as realizations from the posterior distribution with Likelihood L(m*), and
determining and outputting a representation image based on the sample of the posterior distribution, wherein the representation image comprises a representation of the tumor.

2. The computer-implemented image method for reconstruction according to claim 1, wherein the method further comprises that for each subset-image $d_{ss}$, a likelihood L(m) is calculated for each pre-computed set of data in the lookup table, wherein L(m*) is a function L(m*)=f(g(m*)−$d_{ss}$) wherein g(m*) is the data-image d*.

3. The computer-implemented method for image reconstruction according to claim 2, wherein the method further comprises that for each subset-image $d_{ss}$, a probability acceptance $P_{acc}$ is calculated for each pre-computed set of data in the lookup table for the given subset-image $d_{ss}$, based on the likelihood L(m*) for this pre-computed set of data for the given subset-image $d_{ss}$ divided by a maximum likelihood max(L) for the given subset-image $d_{ss}$.

4. The computer-implemented method for image reconstruction according to claim 1, wherein the method further comprises for each subset-image $d_{ss}$ that the probability acceptance $P_{acc}$, calculated for each pre-computed set of data in the lookup table for the given subset-image $d_{ss}$, is used by the extended rejection sampler to determine, whether to accept the model-image m* from the pre-computed set of data in the lookup table for the posterior distribution for the given subset-image $d_{ss}$.

5. The computer-implemented method for image reconstruction according to claim 1, wherein a random value is generated for each pre-computed set of data in the lookup table to compare with the probability acceptance $P_{acc}$ to decide whether to accept the model-image m* from the pre-computed set of data in the lookup table for the posterior distribution.

6. The computer-implemented method for image reconstruction according to claim 1, wherein the method further comprises:
obtaining a noise model for the PET image,
obtaining a modelling error due to using a finite size lookup table, and
using the modelling error to sample the posterior distributions based on the lookup table.

7. The computer-implemented method for image reconstruction according to claim 6, wherein the modelling error is included in the calculation of the likelihood L(m).

8. The computer-implemented method for image reconstruction according to claim 1, wherein determining the representation image comprises calculating a pixel-wise mean of the model-images m of the posterior distribution and outputting the pixel-wise mean of the posterior distribution as the representation image.

9. The computer-implemented method for image reconstruction according to claim 1, wherein determining the representation image comprises determining the most likely pixel intensity for pixels of the representation image based on the pixel intensities for the model-images m in the posterior distribution, and wherein the representation image is based on the most likely pixel intensities.

10. The computer-implemented method for image reconstruction according to claim 1, wherein determining the representation image comprises determining the probability of pixels with a pixel intensity higher than a selected intensity for the representation image based on pixel intensities for the model-images m in the posterior distribution, and wherein the representation image is based on probability of pixels with a pixel intensity higher than a selected intensity.

11. The computer-implemented method for image reconstruction according to claim 1, wherein only a centre pixel intensity, or a group of centre pixels intensities, for the model-images m in the posterior distribution is used for generating the representation image.

12. A medical imaging device comprising a processor, wherein the processor is configured to:
  construct a lookup table of pre-computed sets of data based in part on image data comprising at least one of: tumors, metastases, or a cell structure associated with tumor growth;
  store the lookup table;
  obtain the lookup table of pre-computed sets of data, each pre-computed set of data comprises a model-image m* from a sample M* and a corresponding data-image d*, the model-image m* is a realization from a prior $\rho(m)$, the prior $\rho(m)$ is a statistical model based on expert data, each model-image m* is a representation of an image of one, or more, pixels, the data-image d* is determined based on the model-image m* in the same set of data, each data-image d* is a representation of one or more pixels,
  obtain a PET image and dividing the PET image into subset-images $d_{ss}$, each subset-image $d_{ss}$ is a representation of one or more pixels,
  using, for each subset-image $d_{ss}$ from the PET image, an extended rejection sampler to accept model-images m* from the lookup table representing a posterior distribution given the subset-image $d_{ss}$, wherein using the extended rejection sampler comprises computing a likelihood function for all m* accepted from the lookup table, and accepting them as realizations from the posterior distribution with Likelihood L(m*), and
  determining and outputting a representation image based on the sample of the posterior distribution, wherein the representation image comprises a representation of the tumor.

13. A medical imaging device comprising one or more non-transitory data storage means including machine-readable instructions in communication with one or more processors, wherein the one or more processors execute the machine-readable instructions to at least control a medical image device according to claim 12.

* * * * *

UNITED STATES PATENT AND TRADEMARK OFFICE
CERTIFICATE OF CORRECTION

| | |
|---|---|
| PATENT NO. | : 12,307,559 B2 |
| APPLICATION NO. | : 17/906726 |
| DATED | : May 20, 2025 |
| INVENTOR(S) | : Thomas Mejer Hansen |

It is certified that error appears in the above-identified patent and that said Letters Patent is hereby corrected as shown below:

In the Claims

In Column 18, Claim 2, Line 27, delete "computer-implemented image method for reconstruction" and insert --computer-implemented method for image reconstruction--.

Signed and Sealed this
Seventh Day of October, 2025

John A. Squires
*Director of the United States Patent and Trademark Office*